United States Patent [19]

Risdal

[11] 4,433,587
[45] Feb. 28, 1984

[54] SAMPLER FOR FLOWING PRESSURIZED DRY MATERIAL

[75] Inventor: Norton W. Risdal, Dallas, Tex.

[73] Assignee: Gustafson, Inc., Dallas, Tex.

[21] Appl. No.: 458,478

[22] Filed: Jan. 17, 1983

[51] Int. Cl.³ ............................................. G01N 1/20
[52] U.S. Cl. .............................. 73/863.54; 73/863.52; 73/863.83
[58] Field of Search ............ 73/863.52, 863.54, 863.55, 73/863.81, 863.83, 863.85

[56] References Cited

U.S. PATENT DOCUMENTS

| | | | |
|---|---|---|---|
| 1,966,712 | 7/1934 | Fisher et al. | 73/863.54 |
| 2,370,260 | 2/1945 | Robisch | 73/863.54 |
| 3,066,539 | 12/1962 | Coker et al. | 73/863.54 |
| 3,217,547 | 11/1965 | Cordell et al. | 73/863.57 |
| 3,295,171 | 1/1967 | Strange et al. | 73/863.52 |
| 3,319,469 | 5/1967 | Hartung | 73/863.83 X |
| 3,383,924 | 5/1968 | Cordell | 73/863.83 |
| 3,442,138 | 5/1969 | Hensel | 73/863.83 |
| 3,555,910 | 1/1971 | Spence et al. | 73/863.83 |
| 3,659,461 | 5/1972 | Thompson | 73/863.54 |
| 3,673,700 | 7/1972 | Schalbel | 73/863.83 X |
| 3,747,411 | 7/1973 | McDermot et al. | 73/863.54 |
| 4,082,004 | 4/1978 | Weber et al. | 73/863.54 |

FOREIGN PATENT DOCUMENTS

| | | | |
|---|---|---|---|
| 50084 | 10/1965 | Poland | 73/863.52 |
| 134910 | 1/1961 | U.S.S.R. | 73/863.83 |

Primary Examiner—Gerald Goldberg
Assistant Examiner—Tom Noland
Attorney, Agent, or Firm—Peterson, Palmatier, Sturm, Sjoquist & Baker

[57] ABSTRACT

A sampler for dry material flowing under pressure in a flow duct including a tubular housing, mounting an air cylinder, the piston rod of which connects to a sample tube which is extendible from the housing and into the flow line, the sample tube having a plug forming an obstruction in its rear portion, the forward portion of the sample tube having a material receiving slot in one side facing upstream in the flow duct, and a bleed port on the downstream side of the sample tube adjacent the receiving slot, the sample tube having a discharge port adjacent the front face of the plug in the sample tube and aligned with an outlet opening in the tubular housing and with an outlet spout to which a sample collecting container may be attached, and a seal in the tubular housing spanning entirely across the receiving port and discharge port and the space therebetween on the sample tube and confronting the fluid pressure in the sample tube as the sample tube is withdrawn, until the discharge port opens to the outlet opening at the side of the housing.

20 Claims, 6 Drawing Figures

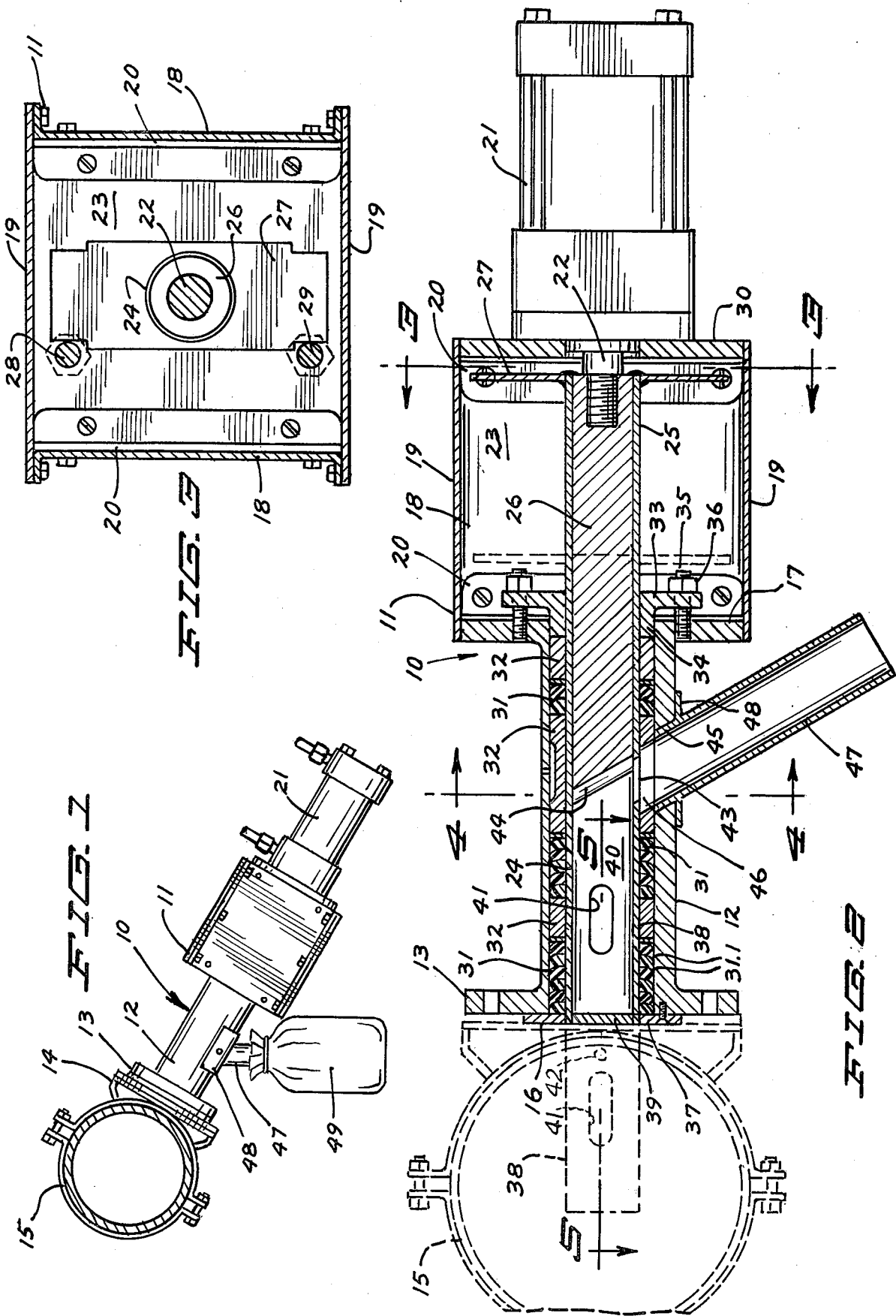

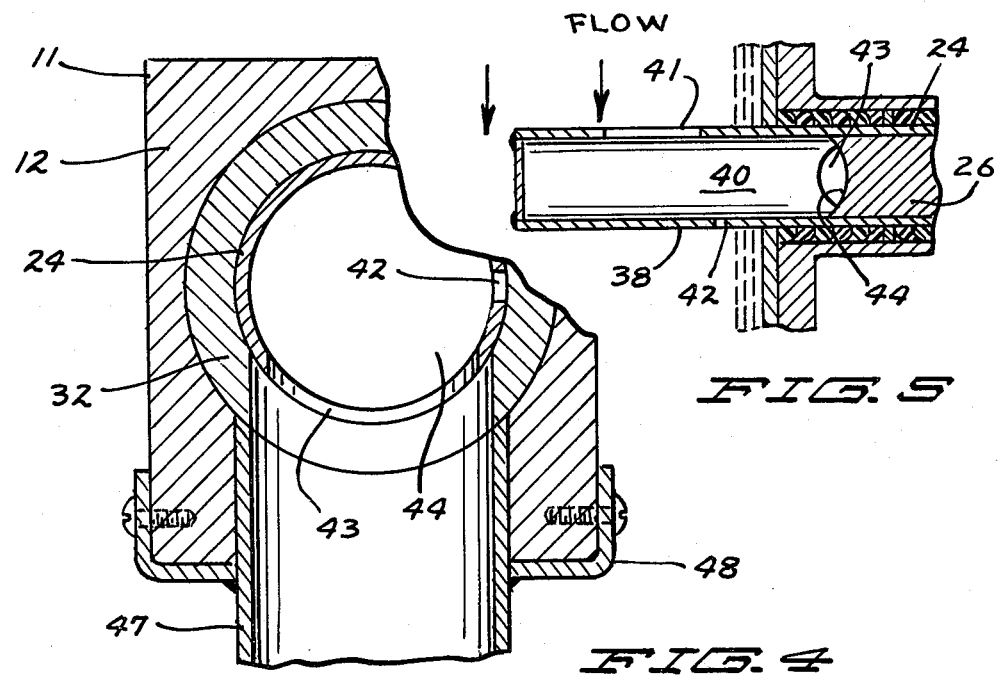
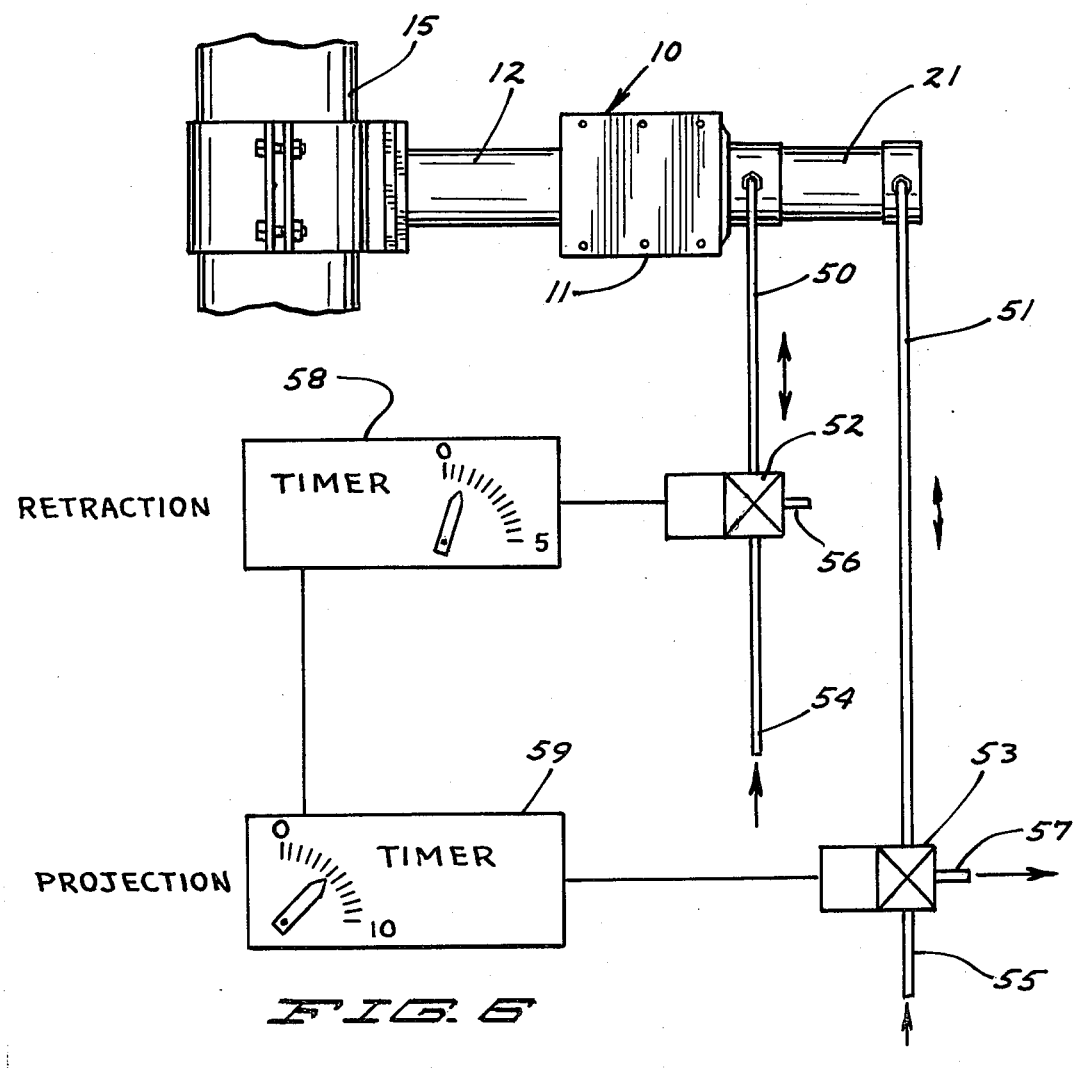

SAMPLER FOR FLOWING PRESSURIZED DRY MATERIAL

This invention relates to samplers for collecting and withdrawing samples of material flowing under pressure as a fluid in a duct or spout.

BACKGROUND OF THE INVENTION

Samplers for many types of materials have been previously known. Such samplers have previously used sample tubes which are projected into and withdrawn from the flow line to collect a sample of the flowing material which may be removed from the sample tube by an auger. In some samplers the sample tube simply allows the collected material to flow by gravity longitudinally through it and be deposited into a sample container. If the flowing material is under fluid pressure, the sample container is under the same pressure. The pressure in the sample container contributes to loss of sample and loss of dust into the atmosphere adjacent the sampler. This type of sampler will accommodate up to 15 psi pressure in the flow line.

In other samplers, the sample tube is replaced by a long head or pelican which may travel or swing across the flowing stream of materials and the collected sample is dropped by gravity into a sample container.

In still other samplers, the sample tube does not move longitudinally, but merely revolves in the flow stream to collect a sample through a slot in the tube, and then discharge the sample along the tube by gravity.

SUMMARY OF THE INVENTION

An object of the invention is to provide a new and improved sampler of dry materials which is simple and inexpensive of construction and operation.

Another object of the invention is to provide a novel sampler for dry material flowing rapidly, but for only a short period of time and under significant fluid pressure.

A principal feature of the invention is a sampler with an inclined sample tube which is alternately projected upwardly into and withdrawn downwardly from the stream of flowing material. The tube has a slot in the upstream side and a small bleed port at the downstream side. The tube has an obstruction spaced from the slot preventing flow along the tube. At the obstruction in the sample tube, the sample tube has a discharge port in its bottom side.

The sample tube is embraced by a number of seals which permit it to be easily slidably projected and withdrawn. The tube seals are confined within a housing which is clamped to the flow duct or spout confining up to 100 psi of fluid pressure and the stream of flowing material. Preferably the sample tube and housing extend downwardly from the flow duct at an oblique angle, which may be between 30 degrees and 60 degrees from horizontal.

When the sample tube is extended, or projected obliquely upwardly into the pressurized flow duct and material stream, both the slot and the bleed port are open, and the discharge port is closed and obstructed by the annular seals within the housing.

The seals and housing have aligned outlet ports which communicate with an adjacent sample spout to which a sample container may be connected. Fluid pressure at the outlet ports and in the sample container remains at atmospheric pressure. When the sample tube is withdrawn from the flow duct, the discharge port in the tube opens into the outlet ports of the seal and housing for discharging the collected sample of flowable material.

The positions and spacings of the slot and discharge port in the sample tube relative to the flow duct and the outlet ports in the housing and seals, are arranged to confine the fluid pressure of the flow duct within the sample tube during retraction of the sample tube until the slot and bleed port are completely closed. As the discharge port in the tube is opened to the outlet of the housing, the fluid pressure in the sample tube suddenly escapes with a "puff" and carries the entire sample with it.

The sample tube is projected and withdrawn by an air cylinder wich is controlled by a cycle timer regulating the frequency of operation, and by a sample timer regulating the residence time of the sample tube in the flow duct.

The sampler has the advantage of being able to take samples, frequently and rapidly of dry materials flowing for only a short time under pressure, and thereby obtain a truly representative composite sample. Although the sample tube may extend into the flow duct and material stream for less than a second, a significant sample will be collected. During sample collection, the slot is open to receive the dry flowing material, and the bleed port is also open in the duct to allow escape of air from the sample tube.

The sample tube may or may not be entirely filled each time it is projected into the flow duct. The time of residence of the sample tube in the flow duct, and the density and rate of flow in the duct will all affect the size of sample collected.

A typical use of the sampler is in preparing oil well cement, which requires very critical blends of portland cement and chemical additives. In certain blends, an error of a few tenths of one percent of certain additives may make the whole batch or blend useless and may endanger an entire well. Cement blending plants use fast loading rates and may load a small 50 sack batch of cement blend into transporting trucks in less than two minutes.

With the present invention a composite sample of 11 to 14 pounds of cement blend may be collected from such a 50 sack batch or lot of blend during the one to two minute loading time. In another sampling operation, a sample of 24.5 pounds was obtained from a 100 sack lot of cement blend which was loaded in approximately one minute.

A sample may be taken as often as once every second or once every second and a half. Residence time of the sample tube in the flow duct is typically on the order of three-fourths of a second. Composite samples of 11 to 14 pounds, taken in 30 to 60 increments of small 50 sack lots may be taken.

During sampling, dust is confined to improve working conditions at the sampler. Product loss is reduced since only the desired quantity of sample is collected. Use of this sampler reduces labor costs as compared to prior methods used. Clean-up time and effort is minimal. Accurate sampling of oil well cement blends may prevent mistakes and accidents that otherwise might cost hudreds of thousands of dollars.

BRIEF DESCRIPTION OF THE DRAWINGS

FIG. 1 is an elevation view of the invention, shown attached to a flow duct from which the sample will be collected;

FIG. 2 is a longitudinal section through the sampler and showing the sample tube projected in dotted lines;

FIG. 3 is an enlarged detail section view taken approximately at 3—3 in FIG. 2;

FIG. 4 is an enlarged detail section view taken approximately at 4—4 in FIG. 2;

FIG. 5 is a detail section view taken approximately at 5—5 in FIG. 2, and showing the sample tube in extended position, and FIG. 6 is a schematic block diagram illustrating the control functions related to the sampler.

DETAILED SPECIFICATION

One form of the invention is illustrated in the drawings and is described herein.

The sampler is indicated in general by numeral 10, and includes a housing 11 of generally tubular form. The front end portion 12 of the housing is formed of cast metal. The exterior configuration is substantially rectangular, and the interior is circular or cylindrical. The front end 12 of the housing has a front flange 13 which mounts an attaching bracket 14 for mounting on a substantially horizontal flow duct 15 in which dry material is flowing under significant fluid pressure in excess of 15 psi and up to approximately 100 psi. At the mounting of the sampler 10, the duct 15 has an opening therein, and a suitable sealing gasket 16 seals around the periphery of the opening end duct 15 to prevent escape of fluid pressure.

A rear flange 17 of the tubular cast front end 12 of the housing faciliates mounting of side plates 18 and top and bottom plates 19 through the use of angle iron clips 20, all of which are bolted together and securely fastened by screws to the flange 17. The housing 11 also mounts an air cylinder 21. The piston rod 22 of the air cylinder is extendible and retractable into the chamber 23 confined by the plates 18 and 19.

A elongate sample tube 24 is confined within the housing 11. The rear portion 25 of the sample tube has an elongate rigid plug 26 affixed therein as by welds. The plug 26 obstructs the sample tube and provides for attachment of the piston rod 22 to the sample tube by threadably receiving the end of the sample tube 22 in a tapped aperture in the rear end of the plug. The rear end of the sample tube has a guide plate 27 affixed thereto as by welding and traversing the interior of the chamber 23 confined by the plates 18 and 19. A pair of stationary guide rods 28 and 29 extend longitudinally through the chamber 23, adjacent the guide plate 27, and are affixed in the end flange 17 and in the end plate 30 which is affixed as by screws to the plates 18 and 19 and also to the air cylinder 21. The stationary guide rods 28 and 29 permit the guide plate to travel therealong as the piston rod of the air cylinder is extended and retracted as to also project and retract the sample tube 24 and prevent the sample tube from turning or rotating as it is longitudinally moved.

In the forward tubular portion 12 of the housing the sample tube 24 is embraced and guided by seals 31 and by bushings or sleeves 32 which are in end-to-end relation with each other within the tubular portion 12 of the housing. The seals 31 and bushings 32 are pressed endwise against each other by a clamp plate 33 which has an annular boss 34 thereon and bearing against the endmost bushing 32. The clamp plate 33 is adjustably secured to the end flange 17 by threaded studs 35 extending through holes in the clamp plate 33 and retained thereon by adjustable nuts 36. The other end of the stack of seals and bushings, 31 and 32 respectively, is retained by the retainer plate 37 which is affixed to the front end of the housing 12 as by screws and which cooperates with the gaskets 16 in providing a sealed relationship between the housing and the duct 15.

The seals 31 are, as illustrated, formed of a multiplicity of Teflon sealing rings 31.1 stacked upon themselves and embracing the outer periphery of the sample tube 24.

The front sample collecting end 38 of the sample tube has an end wall 39 welded therein so that the sample tube defines an essentially closed sample collecting chamber 40 therein. The front or upper sample collecting end 38 of the sample tube has a sample-receiving slot or port 41 formed in one side thereof, to face upstream into the flow in the duct 15 for receiving small quantities of the material being sampled therethrough.

The front collecting end of the sample tube also has a bleed port 42 through the side thereof which is opposite the sample receiving port 41, as to face downstream in the flow duct 15 and to allow escape of air from the chamber 40, whereby to permit the accumulating of a quantity of the dry material flowing in the duct 15. It will be recognized that the bleed port 42 is substantially smaller than the receiving slot 41, and that the bleed port 42 is located adjacent the receiving port 41 as to be opened to the interior of the flow duct 15 when the sample tube 24 is extended or projected into the duct. Both the receiving port 41 and the bleed port 42 are entirely closed by the seals 31 when the sample tube 24 is withdrawn from the duct 15 and into the sampler housing.

The sample tube 24 also has a discharge port 43 in the lower side thereof and located immediately adjacent the front face 44 of the obstructing plug 26 in the sample tube. The discharge port 43 is relatively large and the area of the port 43 is of the same order of magnitude as the cross sectional area of the interior of the sample tube 24.

It will be seen that the front face 44 of the plug 26 is obliquely oriented with respect to the sample tube 24 so as to obliquely confront the discharge port 43, as well as the sample-collecting chamber 40. The front face 44 of the plug 26 is also smoothly curved as seen in FIG. 5 to generally follow the curvature of the periphery of the discharge port 43.

The tubular front portion 12 of the housing also has an outlet opening 45 therein at its bottom side and adjacent the discharge port 43 when the sample tube 24 is in its fully retracted position. The adjacent bushing 32 also has an outlet opening 46 aligned with the opening 45 to carry the samples of material discharge from port 43. A sample delivery spout 47 extends from the outlet opening 45 at an oblique angle with respect to the tubular portion 12 of the housing, and is mounted thereon by a bracket plate 48 to which it is welded.

As illustrated in FIG. 1, the sampler is to be mounted at an oblique angle below the level of the duct 15. The sampler and the sample tube 24 are preferably oriented within the range of 30 degrees to 60 degrees from the horizontal. When the sampler is so oriented, the sample delivery spout 47 will be oriented so as to extend almost directly downwardly and a sample container or bag 49 may be secured to the spout 47 to collect the composite sample of material derived from the material flowing in the flow duct 15.

The air cylinder 21 is a double-acting cylinder, and both ends of the cylinder are connected to air lines 50 and 51, respectively, for alternately supplying air under pressure and allowing the air to escape. Air flow in the lines is controlled by solenoid valves 52 and 53 which are connected with pressure lines 54 and 55, and which have escape ports 56 and 57. The solenoid valves 52 and 53 are respectively controlled by separate timers 58 and 59, respectively. The timer 59 controls the application or air to the cylinder for projecting the sample tube 24 into the flow duct 15, and controls the frequency of the sampling cycle by sampler 10. The timer 58 controls the application of air to the air cylinder for retracting the piston rod and sample tube 24 from the flow duct 15 and therefore controls the residence time of the sample tube 24 in the flow duct. The sampler may be operated over a wide range of frequencies, and particularly, the sampler 10 will take a sample from the flow duct 15 every three seconds, but by adjusting the timer 59, the frequency of sampling may be varied from approximately one second to ten seconds.

The residence time of the sampler tube 24 in the flow duct 15 may be varied by the timer 28 up to approximately five seconds, and typically, the timer will be adjusted to allow the sample tube 24 to be extended approximately three-fourths of a second.

It is important to understand in the operation of the sampler 10, that the seals 31 have sufficient length within the tubular portion 12 of the housing as to span entirely across the sample-receiving slot 41, bleed port 42, and discharge port 43 and all of the space therebetween along the length of the sample tube so that all three of these ports are simultaneously closed to prevent loss of fluid pressure in the chamber 40 which is the same as the fluid pressure in the flow duct 15.

When the sample tube 24 is extended into the flow duct 15, material flowing in the duct will be received through the slot 41, and the air in the chamber 40 of the sample tube will be rapidly bled off through the bleed port 42 so that there is room within the chamber 40 for a quantity of dry material to collect. While the sample tube 24 is extended into the flow duct, as illustrated in dotted lines in FIG. 2, the discharge port 43 confronts the seal 31 and is entirely closed. Accordingly, none of the material in the chamber 40 of the sample tube is allowed to escape, except very minor quantities through the bleed port 42; and the sample chamber 40 in the sample tube has the same identical fluid pressure therein as is found in the flow duct 15.

When the sample tube 24 is retracted in response to operation of timer 58, the sample tube 24 withdraws in an oblique downward direction, and the bleed port 42 is first closed, and then the receiving slot 41 is entirely closed by the seal 31 so that the entire fluid pressure from flow duct 15 is continued in the chamber 40. An instant after the slot 41 is closed by the seal, the discharge port 43 is opened into the outlet opening 45 of the housing, and the fluid pressure is suddenly allowed to escape through the discharge port 43. The fluid pressure escapes with a puff, and the sample of dry material confined within the chamber 40 is carried with the escaping fluid pressure, together with the effects of gravity on the sample material which is set into motion initially by the puff of the fluid pressure. As a result, the collected sample of dry material in the chamber 40 exits the chamber 40 very rapidly and through the discharge port 43 and is directed into the collecting container or bag 49. The rapidly moving material in the chamber 40, moving toward the discharge port 43 is also guided by the obliquely oriented front face 44 of plug 26 so that the material is entirely discharged through the discharge port 43. Because of the rapid discharge of the material from chamber 40, the sample tube is instantaneously ready again to be extended into the flow duct for receiving another sample.

It will be seen that the sampler 10 provides an elongate housing and a sample tube both oriented at an inclined angle of approximately 30 to 60 degrees from horizontal and below the flow duct which is pressurized significantly up to approximately 100 psi. The sample tube may be frequently projected upwardly into the flow duct and quickly withdrawn to extract a sample of the dry material flowing under pressure. The fluid pressure of the flow duct is confined in the sample tube as the sample tube is withdrawn into the housing, and the entire sample tube is momentarily entirely sealed until the discharge port is suddenly opened into an outlet opening at the side of the housing, whereupon the fluid pressure in the sample tube suddenly escapes with a puff and carries the sample of dry material with it out through the bottom side of the housing. The sample tube has a plug in its rear end, adjacent the discharge port for obstructing the sample tube, and the oblique front face of the plug deflects the sample of material flowing under influence of the released puff of fluid pressure and gravity to direct the sample out through the outlet opening and into the sample collecting container.

I claim:

1. Apparatus for collecting samples of dry material flowing under fluid pressure in a flow duct, comprising an elongate housing with front and rear ends and a longitudinally reciprocable sample tube in the housing and extending at a significant oblique angle from horizontal, the sample tube having an upper sample collecting end to project obliquely upwardly and out of the front end of the housing and into the flow duct to which the housing may be connected, and the sample tube being retractable into the housing from the flow duct, drive means on the housing and connected with the sample tube to rapidly project and retract the tube, the housing having a bottom side with an outlet port therethrough and spaced from the front end of the housing, and an elongate seal in the housing and embracing the slidable sample tube between the front end of the housing and the outlet port, the sample tube having a sample receiving port through one side of the sample collecting end thereof to be opened as the sample collecting end projects out of the housing, and to be sealingly closed as the collecting end is retracted into the housing and seal, the sample tube also having a lower side with a discharge port therein, alternately to be opened into the outlet port of the housing when the sample tube is retracted and to be sealed closed by the seal of the housing when the tube is projected, the sample tube being continuously open and unobstructed between the receiving and discharge ports, the elongate seal spanning across both the receiving port and discharge port during retraction of the sample tube to prevent the receiving and discharge ports from being simultaneously open, and the sample tube having a sealing obstruction transversely thereacross adjacent the discharge port.

2. An apparatus according to claim 1 and the sealing obstruction having a front face oriented obliquely to deflect the collected sample out the discharge port when the port is opened.

3. An apparatus according to claim 1 and the sample tube also having a bleed port in the sample collecting end and adjacent the receiving port and opening into the flow duct when the sample collecting end is projected from the housing.

4. An apparatus according to claim 3 and the receiving port and bleed ports being in opposite sides of the sample collecting end of the sample tube.

5. An apparatus according to claim 3 and the bleed port being substantially smaller than the receiving port.

6. An apparatus according to claim 1 and the discharge port having an open area of the same order of magnitude as the area of the inside of the sample tube.

7. A sampler for collecting a composite sample of dry granular material flowing as a fluid in a flow duct under significant fluid pressure, comprising an elongate housing having an end for mounting on the flow duct and having an elongate reciprocable sample tube therein to project into and retract from the flow duct, drive means for very quickly projecting and retracting the sample tube, the housing having an outlet port therein, the sample tube having a sample collecting end with a sample receiving port therein and the sample tube also having a discharge port therein spaced from the receiving port, the sample tube retracting to align the discharge port with the outlet port of the housing, seal means in the housing between the duct end and the outlet port and embracing the sample tube, the seal means extending along the sample tube and entirely spanning the receiving and discharge ports and the spacing therebetween to confine the fluid pressure in the duct in the sample tube as the sample tube is withdrawn into the housing and until the discharge port is suddenly opened into the outlet port of the housing to allow the fluid pressure in the sample tube to suddenly escape with a puff and carry the sample of material into the housing outlet port.

8. An apparatus according to claim 7 and the sample collecting end of the sample tube also having a bleed port adjacent the sample-receiving port.

9. An apparatus according to claim 7 and a sealing obstruction across the sample tube having a front face oriented obliquely to deflect the collected sample out the discharge port when the port is opened.

10. An apparatus according to claim 7 and the sample tube also having a bleed port in the sample collecting end and adjacent the receiving port and opening into the flow duct when the sample collecting end is projected from the housing.

11. An apparatus according to claim 10 and the receiving port and bleed ports being in opposite sides of the sample collecting end of the sample tube.

12. An apparatus according to claim 10 and the bleed port being substantially smaller than the receiving port.

13. An apparatus according to claim 7 and the discharge port having an open area of the same order of magnitude as the area of the inside of the sample tube.

14. Apparatus for collecting samples of dry material flowing under fluid pressure in a flow duct, comprising an elongate tubular housing inclined from horizontal at 30 degrees to 60 degrees and having an upper front end with means for connection to such a pressurized flow duct, the housing having a bottom side with an outlet opening therethrough and spaced from said front end, and a delivery spout on the housing and extending downwardly from the outlet opening for mounting a sample collecting container, a double-acting air cylinder on the housing and having a piston rod extending longitudinally of the elongate housing to rapidly extend and retract therealong, the air cylinder having time controlled control means producing such extension and retraction, an elongate sample tube in the tubular housing and connected with the piston rod of the air cylinder to be rapidly projected out of the front end of the housing and into the pressurized flow duct and to be rapidly withdrawn from the flow duct and into the housing by the cylinder, the sample tube having an upper sample collecting end open throughout its length and a rear end with an elongate plug entirely obstructing the interior of the tube, the sample collecting end of the sample tube having a first side with an elongate sample receiving slot therein to face upstream in the flow duct and to be opened into the duct as the sample tube is projected from the housing, and the collecting end also having a second side opposite the first side and a bleed port in said second side and to be opened into the flow duct when the sample tube is projected from the housing, the bleed port being significantly smaller than the sample receiving slot, and the sample tube also having a lower side moving along the bottom side of the housing and having an enlarged discharge port in said lower side and spaced longitudinally along the tube from the receiving and bleed ports, the discharge port having an open area of the same order of magnitude as the cross sectional area of the interior of the sample tube, and the discharge port moving into open alignment with the outlet opening of the housing when the sample collecting end of the sample tube is withdrawn from the flow duct and into the housing, the plug in the sample tube having a front face oriented obliquely of the tube and obliquely confronting the discharge port to deflect material trough the port, and an elongate annular seal in the tubular housing and embracing the sample tube in sealing relation, the seal extending between the front end of the housing and the outlet opening and entirely simultaneously spanning across the sample receiving, discharge and bleed ports and the space therebetween to confine the fluid pressure in the duct in the sample tube as the sample tube is withdrawn into the housing and until the discharge port is suddenly opened into the outlet opening of the housing to allow the fluid pressure in the sample tube to suddenly escape with a puff and carry the sample of material into the sample collecting container.

15. A sampler for collecting a composite sample of dry granular material flowing as a fluid in a flow duct under superatmospheric gaseous pressure, comprising an elongate housing having an open upper front end for mounting on the duct and a rear end disposed substantially below the upper front end, the housing also having an elongate reciprocable sample tube therein which is projectible and retractable through said front end to project into and retract from the duct, the housing having a side below said upper front end and with an outlet port therein and spaced from said front end, the sample tube having an upper sample collecting end with a sample receiving port in one side of the collecting end and the sample tube also having a lower end below the upper sample collecting end, the lower end of the sample tube having a discharge port spaced from the receiving port of the sample tube and confronting and communicating with the outlet port of the housing, the interior of the sample tube being open and unobstructed between the receiving and discharge ports, drive means for projecting the sample tube from the upper end of the housing to move the sample receiving port outwardly beyond the upper front end of the housing to receive a sample of granular material and gas under pressure and also for retracting the sample tube, and seal means in the housing between the upper end and the outlet port and embracing the sample tube, the seal means extending along the sample tube and entirely spanning and sealing the receiving and discharge ports and the spacing therebetween to prevent the receiving and discharge ports from being simultaneously open, whereby during retraction of the sample tube carrying a sample of the dry granular material and gas under pressure, alignment of the discharge port in the tube with the outlet port of the housing, releases the gas under pressure which starts the flow of dry material from the sample tube through the discharge and outlet ports.

16. An apparatus according to claim 15 and a sealing obstruction across the sample tube having a front face oriented obliquely to deflect the collected sample out the discharge port when the port is opened.

17. An apparatus according to claim 15 and the sample tube also having a bleed port in the sample collection end and adjacent the receiving port and opening into the flow duct when the sample collecting end is projected from the housing.

18. An apparatus according to claim 17 and the receiving port and bleed ports being in opposite sides of the sample collecting end of the sample tube.

19. An apparatus according to claim 17 and the bleed port being substantially smaller than the receiving port.

20. An apparatus according to claim 15 and the discharge port having an open area of the same order of magnitude as the area of the inside of the sample tube.

* * * * *